United States Patent [19]
Eberwine et al.

[11] Patent Number: 5,958,688
[45] Date of Patent: *Sep. 28, 1999

[54] CHARACTERIZATION OF MRNA PATTERNS IN NEURITES AND SINGLE CELLS FOR MEDICAL DIAGNOSIS AND THERAPEUTICS

[75] Inventors: James Eberwine, Philadelphia; Marc Dichter, Penn Valley; Kevin Miyashiro, Philadelphia, all of Pa.

[73] Assignee: The Trustees of the University of Pennsylvania, Philadelphia, Pa.

[*] Notice: This patent issued on a continued prosecution application filed under 37 CFR 1.53(d), and is subject to the twenty year patent term provisions of 35 U.S.C. 154(a)(2).

[21] Appl. No.: 08/848,131

[22] Filed: Apr. 28, 1997

Related U.S. Application Data

[63] Continuation-in-part of application No. 08/334,254, filed as application No. PCT/US95/14792, Nov. 11, 1995.

[51] Int. Cl.$^6$ .............................. C12Q 1/68; C12P 19/34; C07H 21/04
[52] U.S. Cl. ..................... 435/6; 435/91.21; 435/91.51; 536/23.5; 536/24.31; 536/24.33
[58] Field of Search ....................... 435/6, 91.21, 91.51; 536/235, 24.31, 24.33; 935/78

[56] References Cited

U.S. PATENT DOCUMENTS

| | | | |
|---|---|---|---|
| 5,416,197 | 5/1995 | Raper et al. | 530/387.9 |
| 5,447,939 | 9/1995 | Glasky et al. | 514/310 |
| 5,459,037 | 10/1995 | Sutcliffe et al. | 435/6 |
| 5,487,970 | 1/1996 | Rowley et al. | 435/6 |

OTHER PUBLICATIONS

Craig, A. et al., "The Distribution of Glutamate Receptors in Cultured Rat Hippocampal Neurons: Postsynaptic Clustering of AMPA–Selective Subunits," *Neuron* 1993, 10, 1055–1068.

Chicurel, M. et al., "mRNA at the Synapse: Analysis of a Synaptosomal Preparation Enriched in Hippocampal Dendritic Spines," *J. Neurosci* 1993, 13, 4054–4063.

Eberwine et al., "Analysis of gene expression in single live neurons", *Proc. Natl Acad. Sci. USA* 1992, 89, 3010–3014.

European Chromosome 16 Tuberous Sclerosis Consortium, "Identification and Characterization of the Tuberous Sclerosis Gene on Chromosome 16", *Cell* 1991, 75, 1305–1315.

Green et al., "Loss of heterozygosity on chromosome 16p13.3 in hamartomas from tuberous sclerosis patients", *Nat. Genet.* 1994 6, 193–196.

Gennaro, Alfonso, Ed., *Remington's Pharmaceutical Sciences*, 18th Edition 1990, Mack Publishing Co., Easton, PA.

Liang P. et al., "Differential Display of Eukaryotic Messenger RNA by Means of the Polymerase Chain Reaction," *Science* 1993, 257, 967–970.

Nair, S.M. and Eberwine, J. (1994) in Neurobiology of Steroids, eds. de Kloet, R.E. & Sutante, W. (Academic, San Diego), pp. 314–329.

Tecott et al., "In situ Transcription: Specific Synthesis of Complementary DNA in Fixed Tissue Sections", *Science* 1988, 240, 1661–1664.

Tohyma et al., "Nestin Expression in Embryonic Human Neuroepithelium and in Human Neuroepithelial Tumor Cells", *Lab. Invest.* 1992, 66, 303–313.

Topaloglu, H. and Sarnat, H.B., "Acridine Orange–RNA Fluorescence of Maturing Neurons in the Perinatal Rat Brain", *Anat. Record* 1989, 224, 88–93.

Hinds et al. Nature Genetics. 3:36–43, Jan. 1993.

Eberwine et al. Proceedings of the National Academy of Sciences. 89:3010–3014, Apr. 1992.

*Primary Examiner*—Carla J. Myers
*Attorney, Agent, or Firm*—Law Offices of Jane Massey Licata

[57] ABSTRACT

A method of identifying neurite cDNA clones by determining and comparing mRNA expression in selected neurites is provided. cDNA clones identified by this method are also provided. In addition, methods of profiling mRNA expression and diagnosing and treating conditions associated with a pattern of mRNA expression by determining an mRNA expression profile in selected cells are provided.

4 Claims, 3 Drawing Sheets

SEQUENCE LISTING (1) GENERAL INFORMATION:

(iii) NUMBER OF SEQUENCES: 31

(2) INFORMATION FOR SEQ ID NO: 1:

(i) SEQUENCE CHARACTERISTICS:
      (A) LENGTH: 200
      (B) TYPE: NUCLEIC ACID
      (C) STRANDEDNESS: SINGLE
      (D) TOPOLOGY: LINEAR (iv) ANTI-SENSE: NO (xi) SEQUENCE DESCRIPTION: SEQ ID NO: 1:

```
CCTGGNACNC AAGCATCTTN CACCGAACCN TCCNAAAGTN CTGGAATTAN         50

AGTATTNAAG TACATCTAAG TAATGNACTG TAAANTNAAA ATTAANTTAA        100

ANTTTCANTN ATTATNAANA TGAGCTTCGT GCATGTAATA TTGTCGNAAC        150

AAAAGGTGCT TNATGGNANC CTTCTAANGT ATAGTCTCTA AAGNCCTGTT        200
```

(2) INFORMATION FOR SEQ ID NO: 2:

(i) SEQUENCE CHARACTERISTICS:
      (A) LENGTH: 434
      (B) TYPE: NUCLEIC ACID
      (C) STRANDEDNESS: SINGLE
      (D) TOPOLOGY: LINEAR (iv) ANTI-SENSE: NO (xi) SEQUENCE DESCRIPTION: SEQ ID NO: 2:

```
AGGGGTCTTG CCAACANTNN AATTCCTTCG GNAGAATGTA AGCNCCATAA         50

GGGCAGGGGC CACATCTACC CACTNACCTN ATGTCCCCAG CGCTTAGCCT        100

AGTGTNTGGA ACATTNAAGG TGCTCAACCC TTTTNTAGAA TNAATAAATN        150

AATGAAGGCA CACAACGTGC CGAANATTTA AANGTATTGG AGATCTTNTN        200

TTTAANATGG NNAAATAGAG AGCCCAGTAT TATTTAAAAT GTCAGCAATG        250

GGCAAGGCTT CAACCCCCAG TCTTCTGGCT TTTGCCATCC AATACATCCC        300

NCTACTTCCC ATCTANAATN ATGCCTTCCT TTGTNTAGTN ATCTTGCTTT        350
```

```
ACCTTTGCNA TTTACCTCGC TCAAGTTCAA CTTTTCAGTN GCAAGCCTTG        400

GCCCNCAAGN CCTGCCGCGG NTCAAAGCCC CCTG                          434
```

(2) INFORMATION FOR SEQ ID NO: 3:

(i) SEQUENCE CHARACTERISTICS:
        (A) LENGTH: 404
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 3:

```
GGGTAGAAAT GTCANTTCCC ATGAAGGGCA GGGGCCACAT CTACCCACTC         50

ACCTNATGTC CCCAGCGCTT AGCCTAGTGT CTGGNACATT GAAGGTGCTC        100

AACCCTTTTG TAGAATGAAT AAATGAATGA NGGCACACAA CGTGCCGAAC        150

ATTTNAANAT ATTGGAGATC TTGTTTTTAA NATGGGAAAA TAGAGAGCCC        200

AGTATTATTT AAAATGTCAG CAATGGGCAA GGCTTCAACC CCCAGTNTTC        250

TGGCTTTTGC CATCCAATAC ATCCCACTAC TTCCCATCTA AAATNATGCC        300

TTCCTTTGTA AAGTNATCTT GCTTTTACCT TTGCNATTAC CTCGCTCAAG        350

TTCACTTTTC AGTAGCAAGC CTGGGCCCAC AAGGCCTGCC NCGGTCAANA        400

CCCT                                                          404
```

(2) INFORMATION FOR SEQ ID NO: 4:

(i) SEQUENCE CHARACTERISTICS:
        (A) LENGTH: 261
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 4:

```
AGGGGTCTTG GAACAAGAAA TGNNNNTNNN NNNNNATCTG CAGGCTGGAA         50

GTCCCAGAGC ACAGTGTCTG CAGGGTNGGN TTCTCCCAAG GCCTCTNTCC        100

TTGCNTTGTA GACGGCCACC TGTNCTCTGT GTCCTCTNAC AGTNNTCCNT        150

CTGTNTNTNT CTNNNTAATA ATCTCCCCTT CATAAAAGGA CACCAGTCAC        200

TCTGGATTAG GGCTCACTCT AGTAGCCTNN TCTAACATCC NTNACCTCTT        250

TNAAGACCCC T                                                  261
```

(2) INFORMATION FOR SEQ ID NO: 5:

(i) SEQUENCE CHARACTERISTICS:
        (A) LENGTH: 141
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 5:

```
AGGGGTCTTN CAGAGGAACA AAGGAATCNC NCTACAGGNC TCTTTNCTNA         50

NTNANGGACA ACNNNAAACA AGTCCTTTAN GCAGGCTAAG GTCTACATGC        100

NTCTNTCCAT GCAAATCCNG AATATGGCTC CCAAGACCCC T                 141
```

(2) INFORMATION FOR SEQ ID NO: 6:

(i) SEQUENCE CHARACTERISTICS:
        (A) LENGTH: 141
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 6:

| | | | | |
|---|---|---|---|---|
| AGGGGTCTTG | CAGAGGAACA | AAGGAATCGC | TCTACAGGTC | TCTGTACTGA | 50 |
| GTGAAGGACA | ACTTCAGACA | AGTNCTTTNA | GCAGGCTAAG | GTCTACATGC | 100 |
| ATCTATCCAT | GCAAATNCAG | AATATGGCTC | CCAAGACCCC | T | 141 |

(2) INFORMATION FOR SEQ ID NO: 7:

(i) SEQUENCE CHARACTERISTICS:
        (A) LENGTH: 489
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 7:

| | | | | |
|---|---|---|---|---|
| AGGGGTCTTG | TCTTGGAGCT | GTGTTAATAC | AGCAAGCACA | GTATGTATAT | 50 |
| TGCATGTNAC | AGATCAATAA | ACATGGTAAG | ACTTTCTAAA | AATNCTTTTA | 100 |
| ATTCACACTT | TACTTAAGAT | TAAGAAACCT | CAAAAACACC | AAAGTGTGGT | 150 |
| AGGGGTGTAG | CAGGGGAGAC | ACAAAAGAAG | AGACAGGAAG | GGGCTGAGAC | 200 |
| CCTAAGCTCC | AGAAGAGGTA | TGTNATAAAA | TGAGTGGGNT | AATAAATTCC | 250 |
| TTGGTGAAGT | ATGTTTTTNA | NCAACAAAAA | AATTGAAGAT | GAATGTTTAT | 300 |
| CCTAGCATGG | TAAAATGTGT | GGTATGAAGG | CAGCACCCAC | TGGTTTTAAG | 350 |
| AGTCTATTAG | TCTGTGAATA | TCTGNTCTCA | CTCAATTATA | ACTAAAGGAA | 400 |
| TAATTTCCTA | GTNTTCAGGA | ATTTGNAAAT | TTCCNCAAAT | GTGCTTTNNG | 450 |
| GNCCAAGGNT | TTTTTCAAGC | CNACNCCCNA | AGCCCCNTG | | 489 |

(2) INFORMATION FOR SEQ ID NO: 8:

(i) SEQUENCE CHARACTERISTICS:
        (A) LENGTH: 422
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 8:

| | | | | |
|---|---|---|---|---|
| AAAACAGGTN | AGGACNCTCN | AAAAATGCCA | NNTNAATTCA | CACTTTACTT | 50 |
| AAGANTATGA | AACCNCAAAA | NCACCAAAGT | NTNGTAGGGG | TGTAGCAGGG | 100 |
| GNGACACAAA | CGAAGAGNNA | GGAAGGGGCT | GNGACCCNAA | GCTCCAGAAG | 150 |
| AGGTATNTNA | TAAAATTAGT | GGGATAATAA | ATNCCNNNGT | GAAGTATGTT | 200 |
| TTTAAACAAC | AAAAAAATNG | ANGATGNATG | TTTANCCTAG | CATGNCNAAN | 250 |
| TGTGTGGTAT | GANGGCAGCA | CCCNCTGGTT | TTAAGAGCCT | ANTAGGCGTG | 300 |
| TNGATANCTG | ATCTCACTCA | NTNNTAGCNN | GNGAAGTACN | TCCTNGNNGT | 350 |
| NCNGAACTTG | TAAATTTTCN | GAAAGGTGTT | TNTGGTNACA | GGTTNTTTNA | 400 |

| | |
|---|---|
| AGCCAATCNC TCAGGNCCCC TG | 422 |

(2) INFORMATION FOR SEQ ID NO: 9:

(i) SEQUENCE CHARACTERISTICS:
        (A) LENGTH: 136
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 9:

| | |
|---|---|
| AGGGGTCTTG TNAGTNAATT GTNACTTTAA TCATTTGGAA ATAACCTTCT | 50 |
| TTNCTNTNAA TATTTNAGGT ATCTNTTTTG TAAACAGCAT ACACAGTAGT | 100 |
| CCCCACTTAG CAGAGGGGGA TAGTTCCAAG ACCCCT | 136 |

(2) INFORMATION FOR SEQ ID NO: 10:

(i) SEQUENCE CHARACTERISTICS:
        (A) LENGTH: 427
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 10:

| | |
|---|---|
| AGGGGTCTTG AGATATAATT CAGGTGCCAC ACAATTTACC ATTTAANGTG | 50 |
| TACAATTCAA TGGTTTTNGG TATATTACAT TATTTACTTT TNAAGCNGTG | 100 |
| GTAAAATATA CATAACATAA AATTNGCCAT TTNAACATTT TAAATGTGCA | 150 |
| ATTCAGTGGC ATTAGTNGTA TTCACAATGT TATGCAACCA TCACCAGTAT | 200 |
| TTNNNTAACT TTTNATCACC CCAAACAAAA ATTCTGTAAC CATTAAGCAG | 250 |
| TAACTNTNTN CTCCTCTNGT CCTGTCTTTG ATAACTTCTA ATCTGTTTTN | 300 |
| NGTCTCTATG AATTNGCCCA TTCTNCTCTG GGGATTTACT AGACATTTNG | 350 |
| TATGAGTGGA ATTATCTAAN ANTGGTNCNT TGCTGTTTGA CTTATTTCAC | 400 |
| CCAGTATAGN ATGTNCAANG CCCCCTG | 427 |

(2) INFORMATION FOR SEQ ID NO: 11:

(i) SEQUENCE CHARACTERISTICS:
        (A) LENGTH: 286
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 11:

| | |
|---|---|
| CATCATGTAA TGACGNNGAA GNAGTGCACA GATTTGGAAA CAGATNAACC | 50 |
| GCAGTCGCCA ATCTNTGACC CTTATTGACT GTNTGATCTT AAGCAAGTTG | 100 |
| CTTAACCTTT CAGAATCTTT NTNCTTTTAA NTNAAATAGG AGAATAGAGT | 150 |
| ACCTAACTGA TAGGTTTNTN GTNAGGGCTT ANTGAGAGAA TGTATGTATG | 200 |
| GTAGCCATTT TCCAAATAAA GNAGCTATTC TCCAATAATG GCTCCCCAGT | 250 |
| AAGCTTTACC TCCTGGTATT CACACCCAAG ACCCCT | 286 |

(2) INFORMATION FOR SEQ ID NO: 12:

```
        (i) SEQUENCE CHARACTERISTICS:
            (A) LENGTH: 305
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 12:

NNGNNTCTTG NTACTAATTA NTAGCAGCAT GAATGCGTAG AGAGAGCACA        50

GATTTGGAAA CAGNTAACCG CAGTCCCAAT CTCTNACCCT TATTNACTGT       100

GTGATCTTAA GCAAGTTGCT TAACCTTTCA GAATCTTTNT TCTTNTAAAT       150

GAAATAGGAG AATAGAGTAC CTAACTGATA GGNTTGTGNT GAGGGCTTAA       200

NTAGAGANTN TATGTATGGT AGCCATTTTC CAAATAAAGC AGCTATTCTC       250

CAATAATGNC TCCCCAGTAA GCTTTACCTC CTGGTATTCA CACCCAAGNC       300

CCCTT                                                        305

(2) INFORMATION FOR SEQ ID NO: 13:

(i) SEQUENCE CHARACTERISTICS:
            (A) LENGTH: 136
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 13:

NNGGGTCTTG TTAGTGAATT GTGACTTTNA TCATTTGGAA ATAGCCTTCT        50

TTTCTNTTAA TATTTTAGGT ATCTNTTTTG TAAACAGCAT ACACAGTAGT       100

CCCCACTTAG CAGAGGGGGA TAGTTCCAAG ACCCCT                      136

(2) INFORMATION FOR SEQ ID NO: 14:

(i) SEQUENCE CHARACTERISTICS:
            (A) LENGTH: 143
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 14:

AGGGGTCTTG GCCTCACATA CAGCAGGTGT CTATAAATNT TTNTTTAATA        50

AATGATTTAT ACTAGTGCAG TTTCACTATC ACAGTTACTT ACCTTTNTNA       100

GTGTGACAAA CACAGTCACT GAAAACCATA CATCAGGACC CCT              143

(2) INFORMATION FOR SEQ ID NO: 15:

(i) SEQUENCE CHARACTERISTICS:
            (A) LENGTH: 511
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO: 15:

AGGGGTCTTG CAGTGATGGT TATNCTACTG ACACCTGGTG ACAAGAATGG        50

GAATTCTCTG ANGTAATCTC AAGTTAAATG TTACCTCATT TTNTTCTATA       100

GGTAATGGAA GCATAACATC ATTTGATTAG CAGATAGGAC AATATTTCTG       150
```

```
CAATTNTCAT CATGGTGGCA CAAGCATCAC ATTTTTNNTN GCCATTGGTA              200

TTTNGATAAA GTTTTCAAAA GTTACTGCAA TTNGTTATCA GAACACTTGG              250

GTACTGTGTT TGCNGATCAG ACAGANGACT ATTAANGCCA AAAGTATTAA              300

NGAGCTAACA AGCAAAGCCA TCCAATACAA GGCATGTTTT NACAANTNAT              350

ATATCTNGTA GGCAGCTTCA AAATTAATAG TTGAAAGTCC AGAAATCACC              400

ACAGGNTATC ATTTGAGGCC TTAAAACATA NCTGGAAATN TTTNTTGAGN              450

ATTAATNCAA AANCCTAAGC NAGGCNATGT TANNNCCTTA GCNTTATTTT              500

NCAGGATGTT T                                                       511

(2) INFORMATION FOR SEQ ID NO: 16:

(i) SEQUENCE CHARACTERISTICS:
        (A) LENGTH: 370
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 16:

ACCAGGGNTC TNGNTCGTGG CCGGGCTTGT GGGTCCAGGC TTGCTACTGN               50

AANGTTGAAC TNGAGCGAGG TAATAGCATA GGTAAAGCAA GATGNCTTGA              100

CAACGGAGGC ATCATTTNAG ATGGGANGTA GTGGGCTGTA TTGGATGGCA              150

AAAGCCAGAA GACTGGGGGT TGAAGCCTTG CCCATTGCTG ACATTTTAAA              200

TAATACTGGG NTCTCTATTT TCCCATCTGA AAAACAAGAT CTCCNGTATC              250

TTAAAAATGT TCGGCACGTT GTNTGCCTNC ATTCATTTAA TTCATTCTAC              300

AAAAGGGTTN ANGCNCCTTC CANTGTGACC CNACACTTGG GATAAGNGNN              350

TGGGGACATN AGGTAAAGTA                                              370

(2) INFORMATION FOR SEQ ID NO: 17:

(i) SEQUENCE CHARACTERISTICS:
        (A) LENGTH: 261
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 17:

AGGGGTNTTG AAAGAGGTAA TGGATGTNAG ATGAGGCTAC TAGAGTGAGC               50

CCTAATCCAG AGTGACTGGT GTCCTTTTAT GAAGGGGAGA TTATAACAAA              100

GACACAGACA GAGGGATGAC TGTNAGAGGA CACAGAGAAC AGGTGGCCGT              150

CTACAAGGCA AGGAGAGAGG CCTTGGGAGA AACCAACCCT GCAGACACTG              200

TGCTCTGGGA CTTCCAGCCT NCAGATATGT GAGAAAATAC ATTTNTTGTT              250

CCAAGACCCC T                                                       261

(2) INFORMATION FOR SEQ ID NO: 18:

(i) SEQUENCE CHARACTERISTICS:
        (A) LENGTH: 169
        (B) TYPE: NUCLEIC ACID
        (C) STRANDEDNESS: SINGLE
        (D) TOPOLOGY: LINEAR
```

(iv) ANTI-SENSE: NO (xi) SEQUENCE DESCRIPTION: SEQ ID NO: 18:

| | | |
|---|---|---|
| AGGGGNCTTG GNAGCCATAT TCTNCATTTC CNTGGANAGA TGCATGTNGA | | 50 |
| CCTTAGCCTG CTAAAAGCAC TTGTTTNCGG NGNTCCNTNA CTNAGTNCAG | | 100 |
| NGNCCGGTNG NGCGNTTCCT GGNCCCCTTT GNAAGACCCN TGGGCTAGAG | | 150 |
| CGGACGAAAT NGTGTNTNA | | 169 |

(2) INFORMATION FOR SEQ ID NO: 19:

(i) SEQUENCE CHARACTERISTICS:
        (A) LENGTH: 386
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 19:

| | | |
|---|---|---|
| AGGGGTCTTG AGGTGATTGA CTTGCAAATA ATCTTGTGCT CTTAAAGCAC | | 50 |
| ATTTTTGGTA AATTTTCAAA TTTCTGAATA CTAGAAATNA TTTCTTTAGT | | 100 |
| TATAATTGAG TGAGATCAGA TATTCACAGA CTAATAGACT CTCAAAACCA | | 150 |
| GTGGGTGCNG CCTTCATACC ACACATTTNA CCATGCTAGG NTAAACATTC | | 200 |
| ATCTTCAATT TTNTNGTTGT TAAAAAACAT ACTTCACCAA GGNATTTATT | | 250 |
| ATCCCACTCA TTTTATCACA TACCTCTNCT GGNGCTTAGG GTCTCAGGCC | | 300 |
| CTTCCTGTCG TCTNCTTTGG TGNCTCCCCT GCTAAANCCC TACCACACTT | | 350 |
| TGGNGTTTTT NAGGGTTTCT NAACCTTAAG TAAAGT | | 386 |

(2) INFORMATION FOR SEQ ID NO: 20:

(i) SEQUENCE CHARACTERISTICS:
        (A) LENGTH: 395
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 20:

| | | |
|---|---|---|
| AGGGGTCTTG AGGTGATTGA NTTGCAAATA ATCTTGTGCT CTTAAAGCAC | | 50 |
| ATTTTTGGTA AATTTTCAAA TTTCTGAATA CTAGAAATTA TTTCTTTAGT | | 100 |
| TATAATTGAG TGAGATCAGA TATTCACAGA CTAATAGACT CTCAAAACCA | | 150 |
| GTGGGTGCTG CCTTCATACC ACACATTTTA CCATGCTAGG NTAAACATTC | | 200 |
| ATCTTCAATN TTTTNGTTGT TAAAAAACAT ACTTCACCAA GGAATTTATT | | 250 |
| ATCCCACTCA TTTTATCACA TACCTCTTCT GGAGCTTAGG GTCTCAGNCC | | 300 |
| CTTCCTGTCT CTNCTTTGGT GTCTCCCCTG CTACANCCNT ACCACACTTT | | 350 |
| GGNGTTTTTG NGGGTTCTTA ATCTTAAGTA AAGTGTGAAT AAAAA | | 395 |

(2) INFORMATION FOR SEQ ID NO: 21:

(i) SEQUENCE CHARACTERISTICS:
        (A) LENGTH: 136
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 21:

```
AGGGGTCTTG GAACTATCCC CCTCTGCTAA GTGGGGACTA CTGTGTATGC        50

TGTTTACAAA ACAGATACCT AAAATATTAA CAGAAAAGAA GGNTATTTCC       100

AAATGATAAA AGTCACAATT CACTAACAAG ACCCCT                      136
```

(2) INFORMATION FOR SEQ ID NO: 22:

(i) SEQUENCE CHARACTERISTICS:
        (A) LENGTH: 237
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 22:

```
AGGGGNCTTG GAACAAAAAA GACTATAAGA TCAGAGGTAA TGAGGTTGGG        50

ATAGAGATAT GTGGATGAAC CTATGAACAC AAAATATAAA GATCTCATGT       100

TTAATGCTCA TATTAATACT CACCAGAAAG CGTAGAATAA CATTGGCTGA       150

GTATGGTGGC TCTTTGAAAG GCTGAGGTGG GAGGNTCACT TGATGCCAGT       200

AGTTTAAGAC CAGCTTGGGC AACATAGCAA GACCCCT                     237
```

(2) INFORMATION FOR SEQ ID NO: 23:

(i) SEQUENCE CHARACTERISTICS:
        (A) LENGTH: 383
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 23:

```
AACTGNNGCT GCANAATTAA GTCCAAAACA GNAAAAGGAA CAAAATATTA        50

AGCTAATTCC ACTCATACAA AATGTCTAGT AAATTCCCAG AGGNGAATGG       100

GCAAATTCAT AGAGACAGAA AACAGATTAG AAGTTATCAA AGACAGGACA       150

AGAGGAGAAC AGAGTTACTG CTTAATGGTT ACAGAATTTT TGTTTGGGGT       200

GATAAAAAGT TATAAAANTA CTGGTGATGG TTGCATAACA TTGTGAATAC       250

AACTAATGCC ACTGAATTGC ACATTTAAAA TGTTAAATGG CAAATTTTAT       300

GTTATGTATA TTTTCCACAG CTTAAAAAGT AATAATGTAA TATNCCAAAA       350

CCCATTGAAT TGTNCACTTT AAATGGGTAA TTT                         383
```

(2) INFORMATION FOR SEQ ID NO: 24:

(i) SEQUENCE CHARACTERISTICS:
        (A) LENGTH: 305
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 24:

```
AGGGGNCTTG GGTGTGAATA CCAGGAGGTA AAGCTTACTG GGGAGCCATT        50

ATTGGAGAAT AGCTGCTTTA TTTGGAAAAT GGCTACCATA CATACATTCT       100

CTCATTAAGC CCTCACAACA ATCCTATCAG TTAGGTACTC TATTCTCCTA       150
```

```
TTTCATTTAA AAGAACAAAG ATTCTGAAAG GTTAAGCAAC TTGCTTAAGA            200

TCACACAGTC AATAAGGGTC AGAGATTGGG ACCTGCGGTT ATCTGTTTCC            250

AAATCTGTGC TCTCTCTACG NATTCATGCT GCTATTAATT AGTATCAAGA            300

CCCCT                                                             305
```

(2) INFORMATION FOR SEQ ID NO: 25:

(i) SEQUENCE CHARACTERISTICS:
        (A) LENGTH: 306
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 25:

```
AGGGGTCTTG GGTGTGAATA CCAGGAGGTA AAGCTTACTG GGGAGCCATT             50

ATTGGAGAAT AGCTGCTTTA TTTGGAAAAT GGCTACCATA CATACATTCT            100

CTCATTAAGC CCTCACAACA ATCCTATCAG TTAGGTACTC TATNCTCCTA            150

TTTCATTTAA AAGANCAAAG ATTCTGAAAG GTTAAGCAAC TTGCTTAAGA            200

TCACACAGTC AATAAGGGTC AGAGATTGGG ACCTGCGGTT ATCTGTTTCC            250

AAATCTGTGC TCTCTCTACG CATTCATGCT GCTATTAATT AGTATCAAGA            300

CCCCTG                                                            306
```

(2) INFORMATION FOR SEQ ID NO: 26:

(i) SEQUENCE CHARACTERISTICS:
        (A) LENGTH: 446
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 26:

```
ANGGGGGNAC TTNACTGTAT GGGTTTNNAG NGACCTNTTT TTTNNNACAC             50

TCAGAAANGG TAAGNAANTG TNATAGNNAA ACTNCNCTAG GATAATCNAT            100

TTTNTTAAAC AAACATTTNT NGACNCCNNN NTGTTNTNTN AGGCCAAGAC            150

CCNCTGGGGT NAGANGTGGG CCCCNACCCG GGGGNGGGGG GCNCCCACCT            200

TTTTTTTNNC CCCNTTTAAN NGNGGGGGGG TTNAATTGCC CCNGTTTTTG            250

GGGGTNAANN NAATNGGGNC CANAAGGANT GTTTTTTCCC NCNGGGGGGA            300

AAAANATTGT TTTTACCCNC GNTTNCNAAA AAATTTCCCT ANNTNATATA            350

TNNNTTGNGG GGTGCCNCNN GAAGNGNNTA TTAAAGAGTT GTTANANNAC            400

CNCTTNGNGG GGGCGCCCNN AATTGGGGGG GGNGGTCNTA CACCTN               446
```

(2) INFORMATION FOR SEQ ID NO: 27:

(i) SEQUENCE CHARACTERISTICS:
        (A) LENGTH: 396
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 27:

```
AGGGGTCTTG GGCCCAGACA GACATGGGTT CAATTTATAG CACTGATAAT             50
```

```
GTATAGCTGT GGGNCCTCGT GCAGTGATTT AACCTCTGAA AGTTTTCTCA            100

CCTTTAAATG GTGAGGAAAA TACTGATGTG AAAAATATAC AAAAGNAAAC            150

ACGCAAAGCA CCTAGCCTTG CTGGAAACAT CAGTTACTCA TGATGNTGAT            200

CATGATGATG CCAATGATAA TNNTGATAAT GGNGTTAATN NTGGTGATGA            250

AGACTGATCA CAGNCTGCCC TTCTTTTTTG NGGAATTTGG GAAATGAAA             300

TCTCTTTGAT TCCCACTAAT GCNTTTAAGC TGTGTCANGC AACNGATGGG            350

TTGGGGAGGT GGATNGGGGT GACTCAATAT TTAGGTNCCT GCNCTT               396
```

(2) INFORMATION FOR SEQ ID NO: 28:

(i) SEQUENCE CHARACTERISTICS:
        (A) LENGTH: 136
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 28:

```
AGGGGTCTTG GAACTATCCC CCTCTGCTAA GTGGGGACTA CTGTGTATGC             50

TGTTTACAAA ACAGATACCT AAAATATTAA CAGAAAAGAA GGNTATTTCC            100

AAATGATAAA AGTCACAATT CACTAACAAG ACCCCT                           136
```

(2) INFORMATION FOR SEQ ID NO: 29:

(i) SEQUENCE CHARACTERISTICS:
        (A) LENGTH: 10
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 29:

```
AGGGGTCTTG                                                         10
```

(2) INFORMATION FOR SEQ ID NO: 30:

(i) SEQUENCE CHARACTERISTICS:
        (A) LENGTH: 18
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 30:

```
AGAGGGGAAT TCCTGGAG                                                18
```

(2) INFORMATION FOR SEQ ID NO: 31:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: LINEAR (iv) ANTI-SENSE: NO (xi) SEQUENCE DESCRIPTION: SEQ ID NO: 31:

```
CTGAGGACCA GGACTCTCTA                                              20
```

CHARACTERIZATION OF MRNA PATTERNS IN NEURITES AND SINGLE CELLS FOR MEDICAL DIAGNOSIS AND THERAPEUTICS

INTRODUCTION

This application is a continuation-in-part of Ser. No. 08/334,254, filed Nov. 3, 1994. This application claims the benefit of priority under 35 U.S.C. 119 to PCT/US95/14792, filed Nov. 11, 1995.

This invention was made in the course of research sponsored by the National Institutes of Health. The U.S. Government may have certain rights in this invention.

BACKGROUND OF THE INVENTION

In recent years there has been great progress in the understanding of the genetic basis of many medical disorders including neuropsychiatric disorders such as those associated with mental retardation. While the genetic defects of such disorders are disparate and each mechanism appears to be novel, the unifying theme behind the development of these diseases is cellular development and maintenance of cellular networks. For example, for neuropsychiatric disorders the development of these diseases results in part from abnormal brain development and maintenance of neuronal networks.

Neurological networks are made up of individual neurons, each neuron being a separate structural and functional cellular unit. Neurons have special features for the reception of nerve impulses from other neurons, the effect of which may be either excitation or inhibition, and conduction of nerve impulses. Neurons commonly have long cytoplasmic processes known as neurites which end in close apposition to the surfaces of other cells. The ends of these neurites are called synaptic terminals and the cell-to-cell contacts they make are known as synapses. The neurites in higher animals are usually specialized to form dendrites and axons which conduct impulses toward and away from the cell body, respectively. The arrival of an impulse at a terminal triggers the process of synaptic transmission. This event usually involves the release of a chemical compound from the neuronal cytoplasm invoking a response in the postsynaptic cell. Neurons of the central nervous system consist of discrete segments including the cell body, the dendrites and the axon. While most nerve cells conform to this basic structure, there is a wide range of structural diversity based upon the specific function of the cell within the body.

It has been shown that these polarized cells contain a variety of cytoplasmic and membrane-bound proteins differentially distributed throughout the axon, dendrites, and cell body of the neuron. It is believed that neurons of the central nervous synthesize proteins locally, at or near postsynaptic sites which are independent of the cell body. Ultrastructural studies have revealed that polyribosomes are preferentially located either beneath post-synaptic sites or occasionally associated with membrane specializations on dendrites. It has been suggested that these anatomical structures represent the protein synthetic machinery necessary to translate and post-translationally modify different classes of protein in neurons. An energy-dependent mechanism for the selective transport of RNA in neurons has also been shown. The nature and distribution of the RNAs present in these cells, however, is poorly understood.

In situ hybridization (ISH) studies have been successful in identifying very few mRNAs in neuronal processes. Studies using in situ hybridization and Northern blot analyses of synaptosomal RNA fractions with the AMPA-GluR1, -GluR2, GluR3 and GluR-4 and kainate-sensitive GluR5 and GluR6 receptor subunits failed to reveal mRNAs at dendritic locations. (Craig, A. et al., Neuron 1993, 10, 1055–1068; Chicurel, M. et al. J. Neurosci 1993, 13, 4054–4063).

Microdissection of individual neurites has now revealed a large number of mRNAs, including members of the glutamate receptor family, second messenger components, and components of the translational control apparatus, present in hippocampal neurites.

It has now been found that the profiles of expressed mRNAs from discrete segments of the same neurons have different characteristics. These differences in expressed mRNA can be used as a means to specifically target discrete segments of the neuron and to identify and diagnose genetic neurological disorders at the molecular level. Characterization of multiple mRNAs in single cells can also be useful in diagnosis and treatment of neurological disorders and other diseases.

SUMMARY OF THE INVENTION

An object of the invention is to provide a method of identifying neurite cDNA clones which comprises determining the mRNA expression in selected neurites, comparing the relative levels of mRNA expression, and identifying neurite cDNA clones based on the level of mRNA expression.

Another object of the invention is to provide neurite cDNA clones.

Another object of the present invention is to provide a method of profiling mRNA expression in a selected neurite which comprises converting an mRNA population in a soma or process of a selected neurite into cDNA, making the cDNA double stranded, linearly amplifying the double stranded cDNA into aRNA, and using the aRNA as a probe in reverse phase Northern analysis to produce an mRNA expression profile.

Another object of the present invention is to provide a method of diagnosing a condition associated with an mRNA expression pattern which comprises determining the relative levels of mRNA expression in selected cells associated with a selected condition, comparing the relative levels determined with established controls, and diagnosing a condition based upon the comparison of the mRNA expression levels.

Yet another object of the present invention is to provide a method of treating a condition associated with an mRNA expression pattern which comprises determining the relative levels of mRNA expression in selected cells associated with a selected condition, and altering the relative levels with an effective amount of an agent capable of altering mRNA expression.

BRIEF DESCRIPTION OF THE FIGURES

In FIGS. 1B and 1D, the corresponding soma (HP 3–9 in FIG. 1B; and HP2–13 in FIG. 1D) were isolated. In addition to the large number of mRNAs expressed in some neurites (for example, lane 5 in FIG. 1B), there are some commonly shared PCR products between neurites or neurite segments (closed arrowheads) and between neurites and their cell bodies (open arrowheads). These data were reproduced a minimum of three times. In FIGS. 1A, 1C and 1E, a phase-contrast photomicrograph of the cell and the neurites of interest prior to isolation are shown. Dark bars perpendicular to each process represent the approximate transection point.

DETAILED DESCRIPTION OF THE INVENTION

Figure 1A:
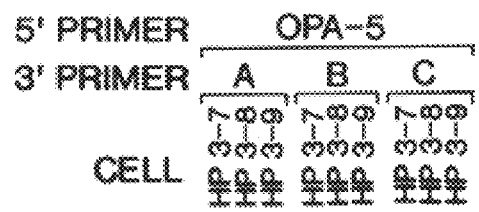
FIGS. 1A–1F are differential displays of three representative cells. A single oligonucleotide, OPA-5, served as the 3'-primer. In combination with three different modified oligo-dT$_{11}$ primers (oligo A, 5'-T$_{11}$AC-3'; oligo B, 5'-T$_{11}$CA-3'; oligo C, 5'-T$_{11}$GC-3'), differential display reactions were carried out on separate neurites (HP3–7 and HP3–8) (FIG. 1B), proximal (HP2–10) and distal (HP2–12) segments of the same process, as well as another separate process (HP2–11) (FIG. 1D), and distal branch points (HP3–5 and HP3–6) of the same process (FIG. 1F) from single hippocampal cells. Each of these neurites were isolated as described in Example 1.

Different regions of the central nervous system are populated by functionally and anatomically distinct synaptic connections. During synapse construction, maintenance and remodeling, it is believed that proteins are selectively transported to these distinct connections. As a result, the specificity of the nervous system is established and modified, at least in part, by these protein targeting mechanisms. It has now been found that mRNA expression profiles are specific for messages seen in neurites. A method has now been developed for identifying neurite cDNA clones by determining the mRNA expression in selected neurites, comparing the relative levels of mRNA expression, and identifying neurite cDNA clones based on the level of mRNA expression.

Isolated hippocampal cells free of overlapping processes from neighboring cells were identified in low density cultures. Under these conditions, neurons grow as isolated cells or in small 2–4 cell groups, either directly on the substrate or on glial cells. Neurons are identified by morphological criteria involving synaptic interactions. Individual proximal and distal neurites were harvested by transecting them at varying distances from the cell body and aspirating them into a micropipette containing the reagents necessary for the first step in the antisense RNA (aRNA) amplification procedure. In a number of cases, multiple processes were isolated from a single cell followed by the aspiration of the cell body. Individual neurites or cell bodies were processed through the following aRNA amplification procedure to produce an mRNA expression profile. The mRNA population in the cell soma or cell process was converted into a complementary DNA (cDNA) using an oligo-dT-T7 primer. After the cDNA was made double-stranded, it was linearly amplified into aRNA using T7 RNA polymerase. For reverse Northern analysis, aRNAs served as a probe for mRNA expression profiles. In subsequent experiments, aRNAs were made into double-stranded cDNAs and used as templates for experiments using the polymerase chain reaction (PCR).

The population of the mRNAs in neurites was assessed initially by mRNA expression profiling. Southern blots containing cloned cDNAs encoding members of the ionotropic glutamate receptor family were probed with radiolabeled aRNA from individual neurites or cell bodies. Glutamate receptors, classified into N-methyl-D-aspartate (NMDA), α-amino-3-hydroxy-5-methyl-isoxazole-4-propionate (AMPA; GluR1–4), and kainate (GluR5–7) subtypes are the primary mediators of excitatory synaptic transmission in the brain. These receptors also play a role in the biochemical events associated with excitotoxicity and long-term potentiation (LTP), a specialized form of synaptic plasticity. The qualitative mRNA expression of multiple members of the glutamate receptor family was examined.

All neurites expressed GluR1, GluR2, GluR4 and NMDAR1 mRNA. In a majority of neurites, mRNA expression of GluR3 (15/19), GluR5 (14/19), was observed; while expression for GluR6 mRNA was detectable in approximately one half the neurites studied. The presence of these subunits was confirmed by subunit specific PCR. In contrast, only one neurite showed detectable hybridization signals for NR2a and NR2c mRNA. Thus, neurite cDNA clones may be identified by determining the mRNA expression for glutamate receptors. Examples of preferred glutamate receptors include, but are not limited to, GluR1, GluR2, GluR3, GluR4, GluR5, GluR6, GluR7, NR2a and NR2b.

A number of neurite cDNA clones have now been identified in accordance with the methods of the present invention. Two of these clones have been found to correspond to farnesyl diphosphate (FPP) synthase mRNA identified in two separate distal processes. As part of the isoprene biosynthetic pathway, FPP synthase generates the farnesyl moiety ultimately transferred to the COOH-terminal CaaX motif of mammalian ras proteins. Two other cDNAs have been found to have sequence similarity with mRNAs for the γ-subunit of the interleukin-2 receptor and the tumor necrosis factor inducible protein A20. The remaining cDNA clones have little sequence similarity with any published gene sequences. By sequencing the cDNA clones corresponding to full-length RNAs, it is possible to identify the role the primary sequence and secondary structural characteristics of the mRNA play as recognition elements in targeting and transport of the mRNA. The cDNA clones of the present invention are identified in Table 1 as SEQ ID NO: 1 through SEQ ID NO: 28.

TABLE 1

| CLONE | SEQ ID NO: |
| --- | --- |
| 57-3 | SEQ ID NO: 1 |
| 59-3 | SEQ ID NO: 2 |
| 60-3 | SEQ ID NO: 3 |
| 63-3 | SEQ ID NO: 4 |
| 64-3 | SEQ ID NO: 5 |
| 65-3 | SEQ ID NO: 6 |
| 66-3 | SEQ ID NO: 7 |
| 67-3 | SEQ ID NO: 8 |
| 68-3 | SEQ ID NO: 9 |
| 70-3 | SEQ ID NO: 10 |
| 71-3 | SEQ ID NO: 11 |
| 72-3 | SEQ ID NO: 12 |
| 73-3 | SEQ ID NO: 13 |
| 76-3 | SEQ ID NO: 14 |
| 78-3 | SEQ ID NO: 15 |
| 60-7 | SEQ ID NO: 16 |
| 63-7 | SEQ ID NO: 17 |
| 64-7 | SEQ ID NO: 18 |
| 66-7 | SEQ ID NO: 19 |
| 67-7 | SEQ ID NO: 20 |
| 68-7 | SEQ ID NO: 21 |
| 69-7 | SEQ ID NO: 22 |
| 70-7 | SEQ ID NO: 23 |
| 71-7 | SEQ ID NO: 24 |
| 72-7 | SEQ ID NO: 25 |
| 74-7 | SEQ ID NO: 26 |
| 78-7 | SEQ ID NO: 27 |
| 100-7 | SEQ ID NO: 28 |

The cDNA clones of the present invention can be used in the diagnosis of neuropsychiatric diseases. Human genes containing unstable triplet repeats are associated with several neuropsychiatric diseases including, but not limited to, Huntington's disease, spinal and bulbur muscular atrophy and spinocerebellar ataxia type 1. These diseases show a variety of clinical symptoms making them difficult to diagnose. However, an understanding of these diseases at the molecular level provides the diagnostic laboratory with the capability to test directly whether an individual's DNA contains the disease-causing mutation, either as a confirmation of a clinical diagnosis or prior to any symptoms. For example, fragile X chromosomes, associated with mental retardation in most males that have it and, to a lesser degree, some of the females heterozygous for it, can be identified using cDNA clones of the present invention having SEQ ID NO: 1 through 15. The cDNA clones of the present invention can also be used in prenatal screening.

Distinct relative variations in mRNA expression have also been identified using reverse Northern blot analysis. Differences in the relative levels of glutamate receptor mRNAs expressed between a neuronal process or processes from the same cell and its cell body have been observed. In a number of cells, the qualitative expression patterns were very similar, yet the relative intensity of the hybridization signal was more profound for specific subunits. For example, relative levels of NMDAR1 and GluR5 mRNA were clearly elevated in HP9a, the apical neurite, versus HP9b, the basal neurite, or the soma. This tendency was complimented in other cells which displayed a more differentiated qualitative pattern of glutamate receptor mRNA expression. This differentiated pattern of mRNA expression contributes to the physiological function of a synapse. These differences in the relative levels of mRNA expression result in the occurrence of different neuronal processes in the same cell. In addition to glutamate receptors, the expression of several other cDNAs has been assessed with reverse Northern blot analysis. Previous reports have demonstrated the dendritic localization of the α-subunits of the $Ca_{2+}$/calmodulin-dependent protein kinase (CaMK II) mRNA. It has now been found that mRNA expression in distal and proximal segments of isolated neurites is strongly positive for CaMK II. Thus, specific segments and processes of a neuron may be targeted by determining the profile of mRNA expression involved in the process, identifying an mRNA with a high level of expression and targeting an agent to that mRNA.

Alzheimer's disease, amyotrophic lateral sclerosis, Huntington's disease and epilepsy are all examples of disorders which involve the degeneration of specific groups of neurons in discrete regions of the nervous system. It appears that different regions of the nervous systems, and specifically, different types of neurons possess different sensitivities to agents. Therefore, to assess the neurotoxicity of an agent, the agent should be assessed in neurons isolated from different regions since it appears that some neuron types are more sensitive than others. It has now been found, however, that neuron types can be identified by determining the mRNA expression in selected neurons, comparing levels of mRNA expression in the selected neurons with levels in known neurons, and identifying the neuron type based on the level of mRNA expression. Thus, the neurotoxicity of an agent for a specific neuron type may be assessed in a culture of mixed neuron types. In this method, it is preferred that mRNA expression is determined by an aRNA amplification procedure.

Figure 1A:
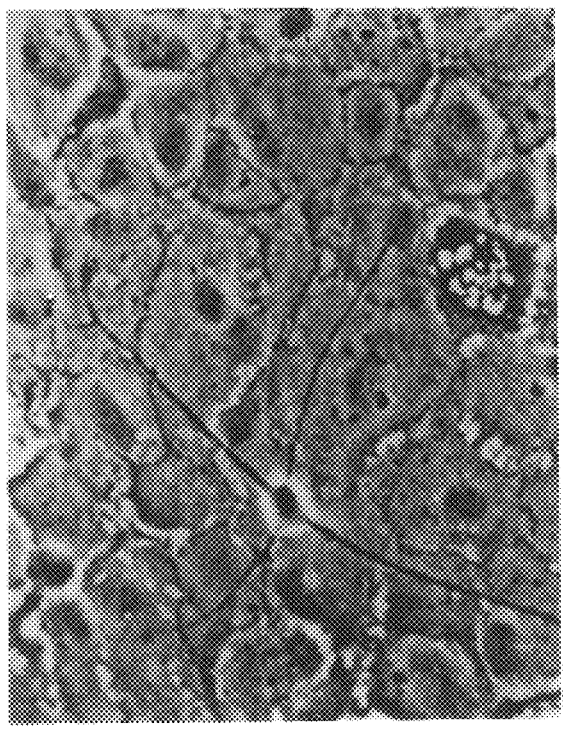
Figure 1B:
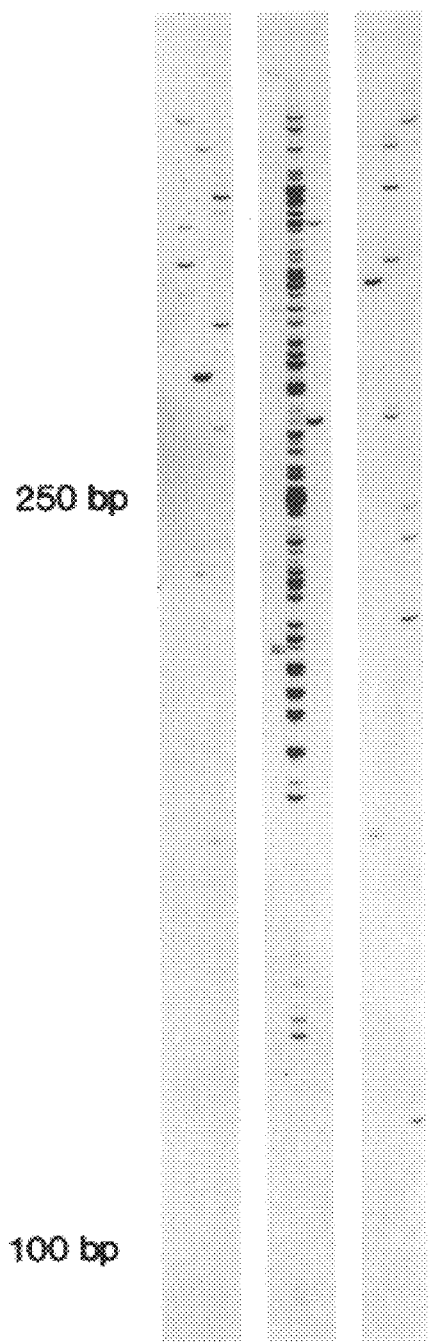
Figures 1C, 1D:
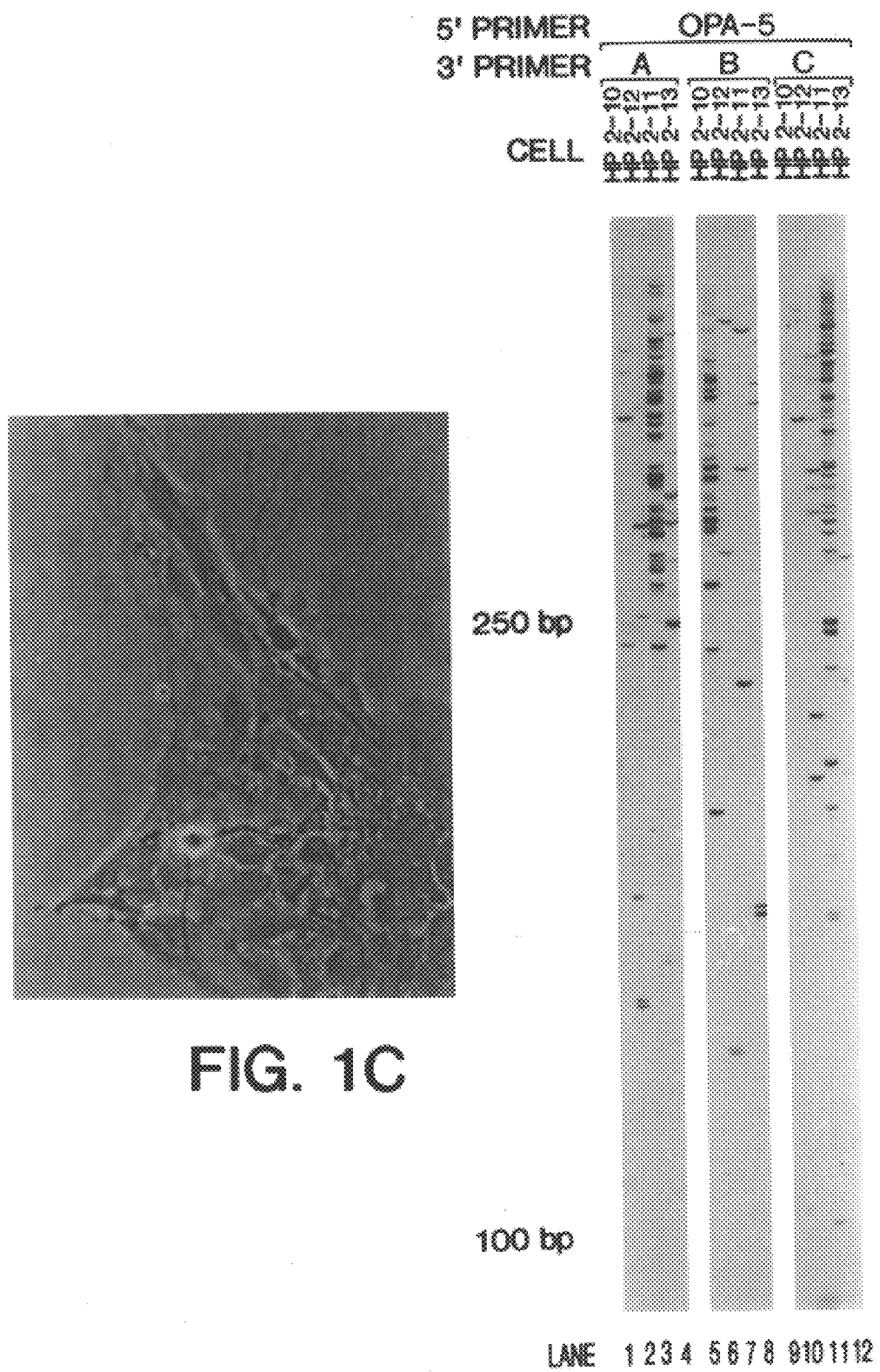
Figure 1E:
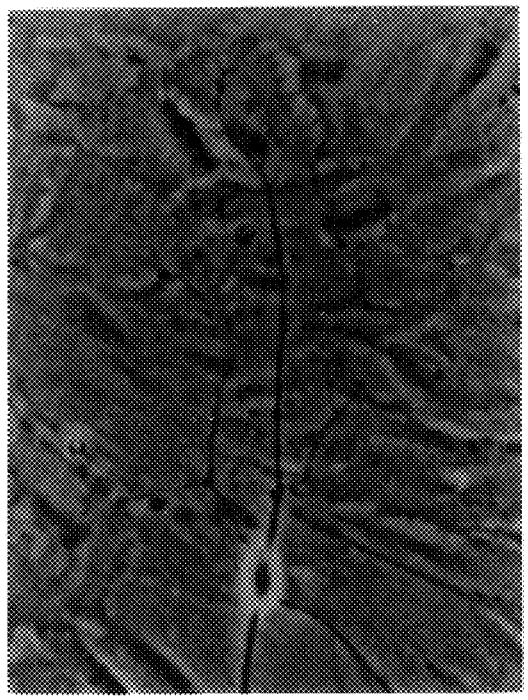
Figure 1F:
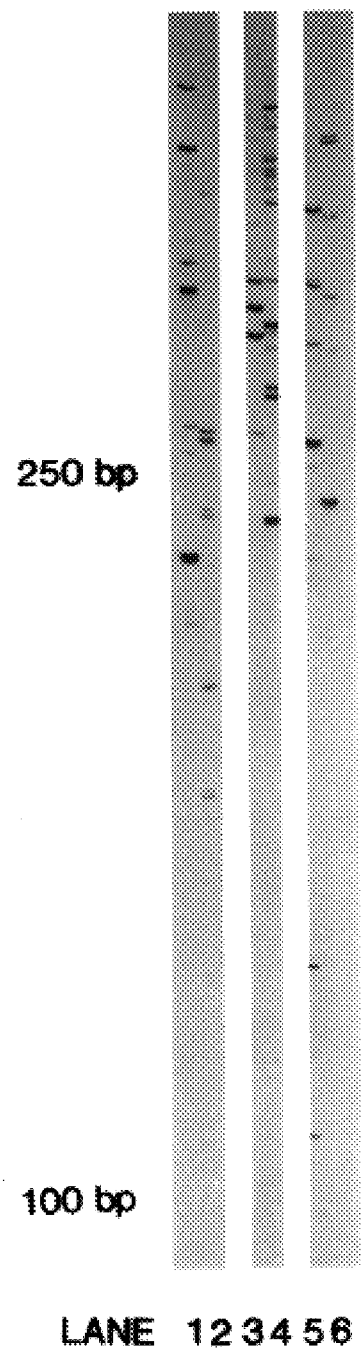

The complexity of mRNA expression in neurons was investigated further using a PCR-based assay, differential display developed by Liang P. et al., *Science* 1993, 257, 967–970. In these experiments, a single 10 mer (OPA-5;5'-AGGGGTCTTG-3', SEQ ID NO: 29) which serves as the 5'-primer and a modified polythymidine primer containing a two base extension were used to amplify specific populations of the polyadenylated RNA pool. In each of these reactions, banding patterns unique to the soma or process and the combination of primers used were observed. Differential display (DD) of mRNAs from three sets of cells are shown in FIG. 1. The complement of DD profile of neurites exhibited a large number of mRNA species. These patterns of PCR products indicate that mRNAs are differentially distributed. For example, in a typical cell in which two neurites are transected and isolated, there are transcripts that migrate at similar molecular sizes between individual neurites. This circumstance is repeatedly seen in proximal and distal segments of the same process and in distal branch points of a single process. While there are some products found concomitantly in one or more neurites and between neurites and their corresponding cell bodies, there are numerous transcripts that are unique to individual neurites or segments of individual neurites. Samples of media and tRNA did not display any banding pattern using differential display.

The contamination of neurites with surrounding glia or astroglial processes was assessed by glial fibrillary acidic protein (GFAP) mRNA. Neurite and soma preparations used in these experiments were determined to be free of GFAP mRNA. The existence of multiple mRNAs in neuronal processes suggests that mRNA transport and local protein synthesis plays a role in the regulation of neuronal physiology, development and regeneration.

In the present invention, mRNA expression patterns or profiles can be used to diagnose conditions related to the presence or absence of synthesized proteins. By "mRNA expression patterns or profiles" it is meant the levels of a variety of selected mRNAs in a selected cell or neurite which are determined in accordance with the method of the present invention. mRNA levels to be profiled can be selected routinely by those of skill in the art in accordance with the condition to be diagnosed. By comparing the mRNA expression profiles in selected cells associated with a neurological disorder or other disease with control cells differences in levels of selected mRNAs can be compared. By "selected cell" it is meant a cell associated with pathologic tissues resulting from or causing the disorder. In a preferred embodiment, for neurological disorders, selected cells refers to the diseased neurons and cells surrounding these neurons such a glia and giant cells. Differences in mRNA expression profiles of selected cells versus control cells can be used in diagnosis of the disorder or disease.

For example, in recent years, several human neurological diseases have been identified resulting from the expansion of trinucleotide repeats. These triplet repeats are normally polymorphic and exonic, though not always coding. In disease states, they become markedly unstable and may expand moderately or by thousands of repeats in a single generation thereby altering gene expression, message stability or protein structure. Thus, in a diseased state, alterations in normal mRNA expression patterns or profiles would be expected.

mRNA expression profiling within single cells provides a powerful tool for studying gene expression and the molecular pathophysiology of many other diseases as well. For example, tuberous sclerosis (TSC) is an autosomal dominant disease which is characterized by mental retardation, epilepsy, and tumors of the skin, retina, heart, kidney and brain. Tubers are regions of focal cerebral cortical dysplasia in TSC which exhibit disorganized or absent cortical lamination and dysmorphic neurons with abnormal dendritic arborization and spine density. It has been hypothesized that disruption of the TSC gene (TSC2) may disrupt differentiation and maturation of neuronal precursors, since the TSC2 gene product is believed to regulate cellular proliferation. Many of the abnormally shaped neurons are stellate or multipolar cells not characteristic of normal cortex. However, tubers are histologically heterogenous lesions containing a variety of cell types. For example, dysmorphic giant cells, which extend short thickened processes are also found in tubers. Accordingly, an issue critical to studying tubers and providing insight into their epileptogenicity is that not all cells within the tuber may be abnormal.

Identifying differences at the molecular level between normal and abnormal cells of the tubers is difficult because homogenization of tuber samples for mRNA analysis would include all cell types in the tuber, thereby precluding any conclusions regarding the molecular composition of only neurons or only giant cells. Further, in situ hybridization or in situ polymerase chain reaction on tissues is extremely time consuming, since only one or two probes can be used at one time. However, using the method of the present invention, poly(A)$^+$ mRNA from immunohistochemically labeled cells in tubers were amplified and detected so that the molecular pathology of single abnormal cells could be assessed. In these experiments, poly(A)+ mRNA was amplified from individual, nestin-labeled giant cells and dysmorphic neurons to identify mRNAs suggestive of cellular immaturity and to detect the TSC2 transcript.

Many mRNAs were detected by reverse Northern blotting with radiolabeled aRNA generated from TSC and control tissue sections. cDNAs were chosen for analysis to provide a representative sample of neuronal and glial cell mRNAs and also to provide corroborative data on proteins detected by immunohistochemistry. mRNAs identified included human nestin, internexin, NFL, NFM, MAP2, CaMKII, GAD65, CX32, trkA, Ca-N, and the glial markers GFAP and CX43. However, mRNA encoding several proteins including $\alpha_2$ and $\alpha_3$ GABA$_A$ receptor subunits and the Ca-L were not detected in TSC or control individuals. The presence or absence of mRNAs from whole sections provided useful information for subsequent single cell-analysis. For example, detection of GFAP mRNA in whole sections but not individual giant cells provided evidence that GFAP mRNA was in fact absent from giant cells and not merely undetectable due to limitations of the mRNA amplification. In addition, neurons and giant cells in cortical tubers were found to express several mRNAs and proteins characteristic of embryonic neuroepithelial precursor cells. These findings suggest a fundamental disruption of neuronal maturation in tubers. It is believed that an existing TSC2 mutation/deletion may disrupt maturation of cortical neuroepithelial cells in association with a postulated somatic TSC2 mutation (European Chromosome 16 Tuberous Sclerosis Consortium *Cell* 1991, 75, 1305–1315; Green et al. *Nat. Genet.* 1994 6, 193–196) which occurs in the ventricular zone prior to cessation of cell cycle activity and onset of neuronal migrations. mRNA characteristics of normal neurons (but not glia) such as CaMKII, GAP43, calcium channel subunits and intermediate filaments were also identified in TSC neurons and giant cells thus indicating that while cells within tubers may retain embryonic features, the expression of many genes was not completely disrupted. It is believed that expression profile differences between TSC and control cells may reflect quantitative and qualitative disregulation of transcription. In fact, subtle differences in the mRNA expression profiles of giant cells and neurons within tubers compared with normal cortical neurons may have substantial developmental effects. These data also suggest the likelihood that there is a heterogenous population of cells within tubers, some of which may be more or less affects by a TSC2 mutation.

Thus, amplification of mRNA in single live neurons or other cells reveals important information regarding relative levels of gene expression. While TSC was studied in the above experiments, the ability to amplify multiple mRNAs from immunohistochemically labeled cells within pathologic material can be used in the study of many neurologic disorders and other diseases. In fact, mRNA has now been amplified in fixed tissues from other neurological disorders such as focal cortical dysplasia and Alzheimer's disease, thus indicating that fixed tissue from a variety of disease states can be studied with this method.

Methods related to diagnosing a condition associated with an mRNA expression pattern comprise determining the relative levels of mRNA expression in selected cells associated with a selected condition; comparing the relative levels determined with established controls; and diagnosing a condition based upon the comparison of the mRNA expression levels. Measuring of mRNA expression patterns as disclosed in the present invention can also be used in methods for treating a condition associated with an mRNA expression pattern. Levels of mRNA expression in selected cells associated with a selected condition are determined and compared to normal levels in the same type of cells. If the level of mRNA expression is abnormal, an effective amount of an agent capable of altering mRNA expression is administered. In this method, it is preferred that the mRNA expression levels be measured in neurons. Examples of agents capable of altering mRNA expression include, but are not limited to, antisense oligonucleotides and pharmacological agents such as dopamine, serotonin and cyclic AMP. Such agents are administered in an effective amount either alone or in conjunction with a suitable pharmaceutically acceptable carrier. By "effective amount" it is meant a concentration of an agent to be administered which is sufficient to modulate expression of mRNA. Such concentrations can be routinely determined by those of skill in the art upon this disclosure and will depend upon the age, weight and condition of a patient. Suitable pharmaceutically acceptable carriers are well known in the art and are described for example in Gennaro, Alfonso, Ed., *Remington's Pharmaceutical Sciences,* 18th Edition 1990, Mack Publishing Co., Easton, Pa., a standard reference text in this field. Pharmaceutical carriers may be selected in accordance with the intended route of administration and the standard pharmaceutical practice.

The following nonlimiting examples are provided for illustrative purposes.

EXAMPLES

Example 1

Preparation of Neurites

Hippocampi were dissected from ED20–21 rat fetuses, dissociated in trypsin and plated at 30,000–100,000 viable cells/ml of media onto poly-lysine covered glass coverslips held in 35 mm tissue culture petri dishes. One day after plating, 0.5 ml of media was replaced with media containing 20 mM potassium. The cultures were subsequently fed once a week with a drop of the high K$^+$ media. Experiments were performed after 21–28 days in culture. Cell bodies and their neurites were taken from cells cultured from different animals on three different days under similar conditions. During each of these sessions, a sample of culture media was also aspirated and processed through aRNA processing to assess the possible presence of mRNAs in the culture media from dying cells.

Example 2

Determination of mRNA Band Patterns

Reactions were carried out in 25 $\mu$l volumes using the Hot Start technique (Perkin Elmer, product #N808-0100) with an upper-lower ratio of 1.5 to 1. Reactions contained 200 μM of dATP, dGTP and TTP, 4 μM dCTP, 5 μCi of $^{33}$P-dCTP or 4 μCi $^{32}$P-dCTP or 18.75 μCi of $^{35}$S-dATP (NEN/Dupont), 0.4 μM of OPA-5 or other 10 mers (Operon Technologies), 0.6 μM of oligo A, B or C, 2.5 mM MgCl$_2$, 1.25 units of AmpliTaq polymerase (Perkin Elmer), and 1 μl of a 1:10 dilution of DNA previously processed through a single round of aRNA amplification. Under these conditions, the primers are in vast excess to the amount of template used for the reaction. Reactions were cycled 35 rounds at 94° C. for 30 seconds, 40° C. for 90 seconds and 72° C. for 45 seconds, followed with a final 5 minute elongation at 72° C. in a Biosycler thermocycler. Approximately 5 μl of the reaction was loaded onto a 6% acrylamide/7 M urea gel. Gels were vacuum dried and apposed to XAR film. Gels shown in FIG. 1 used $^{33}$P-dCTP. The reactions exhibited a banding pattern unique to a sample.

Example 3 cDNA Synthesis

Micropipettes containing reagents for first strand cDNA synthesis also contained 5 μM dithiothreitol and RNAsin (Promega, Madison, Wis.) at 0.5 units/μl. The efficiency of amplification, as based upon trichloroacetic acid precipitated counts and Northern blot analysis to assess the size distribution of mRNAs, did not differ with or without digitonin. Antisense RNA processed through two rounds of amplification was added to Southern blots containing equal amounts (500 ng) of glutamate receptor cDNAs linearized with the appropriate restriction enzyme and applied by vacuum onto a slot blot apparatus. A random-primed vector cDNA clone, pBluescript SK (Stratagene, La Jolla, Calif.) was added to stripped blots to demonstrate the presence of DNA in each slot. Scanning densitometry analysis was performed on autoradiographs using a Scanning Laser Densitometer (Molecular Dynamics, Sunnyvale, Calif.). Hybridization signals were normalized to ribosomal RNA for each neurite or soma studied.

Example 4

Characterization of Multiple mRNAs within Fixed Immunohistochemically Labeled Cells Pathologic Material Cortical tubers from frontal and temporal neocortex were obtained during epilepsy surgery from five unrelated patients ages 2–11 years of age who met clinical criteria for tuberous sclerosis. In three of these cases, a family history of TSC was documented, although formal genetic linkage analysis was not performed. Control samples from frontal and temporal cortex were obtained post mortem from three children (ages 2 months, 4 years and 10 years) without a history of TSC or other neurologic disease who died of nonneurologic causes. Specimens were fixed by immersion in 4% paraformaldehyde/PBS (vol/vol)/70% ethanol/150 mM NaCl (vol/vol), or Bouin's fixative, embedded in paraffin, and cut into 7-μm sections.

Immunohistochemistry (IHC)

Antibody labeling was performed in accordance with procedures described by Tohyma et al. Lab. Invest. 1992, 66, 303–313 utilizing microwave enhancement of paraformaldehyde and Bouin's fixed material. Tissues to be analyzed for mRNA were not microwaved. Sections were labeled with monoclonal antibodies to α-internexin; glial fibrillary acidic protein; microtubule-associated protein 2; MIB-1, which labels an active cell cycle epitope encoded by a repetitive 66-bp Ki-67 element; and PCNA, which is a DNA polymerase or auxiliary factor. MIB-1 and PCNA serve as indicators of non-G$_0$ cell cycle state. Rat tonsillar epithelium exhibited extensive nuclear labeling with both MIB-1 and PCNA antibodies served as positive control for antibody staining. A rabbit polyclonal antiserum (AN-130) that recognizes human nestin was raised against recombinant rat nestin protein expressed in E. coli. Non-microwave enhanced tissue was used for in situ transcription.

To histologically assess RNA in the tissue specimens, sections were stained in accordance with procedures described by Topaloglu, H. and Sarnat, H. B. Anat. Record 1989, 224, 88–93 with fluorochrome acridine orange (AO) which appear orange (absorbing at 470 nm) when bound to RNA. Most giant cells and neurons exhibited strong AO staining, suggesting that RNA had not degraded despite a lengthy fixation and storage period in some specimens.

In Situ Transcription (IST)

Following IHC, Boulin's- and 4% paraformaldehyde-fixed sections were washed in 0.2 M HCl for 20 minutes, rinsed in phosphate-buffered saline (PBS, 7.4) and then placed in proteinase K (50 μg/ml) for 30 minutes. IST was performed on regions characterized by extensive nestin and MIB-1 immunolabeling. AN 11-nt oligo (dT primer coupled to a T7 RNA polymerase promoter sequence (oligo-dT-T7) was hybridized to cellular poly(A)+ mRNA for 12–18 hours with 50% formamide and diethylpyrocarbonate (DEPC)-treated distilled H$_2$O directly on the section as described by Tecott et al. Science 1988, 240, 1661–1664 and Nair, S. M. and Eberwine, J. (1994) in Neurobiology of Steroids, eds. de Kloet, R. E. & Sutante, W. (Academic, San Diego), pp. 314–329. cDNA was synthesized directly on the section with avian myeloblastosis virus reverse transcriptase (0.5 units/μl); Seikagaku America, Rockville, Md.) in IST reaction buffer [10 mM Tris-HCl, pH 8.3/6 mM MgCl$_2$/120 mM KCl/7 mM dithiothreitol/250 μM each dATP, dCTP, dGTP, and dTTP/RNAsin (Promega) at 0.12 unit/μl]. Sections were washed for 8–12 hours in 0.5×SSC. In several sections from each specimen, cDNA from the entire section was extracted with 0.2 M NaOH/1% SDS and mRNA amplification was performed as below. In other sections, individual cells were aspirated. In this way, mRNA amplified from whole sections and individual cells was compared.

Single Cell mRNA Amplification

Following IHC and IST, individual nestin-labeled cells were dissected away from the surrounding neuropil by using a micromanipulator and aspirated gently into glass microelectrode. Nonstained pyramidal neurons in control specimens were visualized by phase contrast microscopy and aspirated. While IST had already been performed on sections to ensure cDNA synthesis, the microelectrodes were filled with buffer (10 mM Hepes buffer, pH 7.4/120 mM KCl/1 mM MgCl$_2$), dNTPs(250 μM each), oligo-dT-T7 primer, and avian myeloblastosis virus transcriptase, and cDNA synthesis was performed for 90 minutes at 40° C. as described by Eberwine et al. Proc. Natl Acad. Sci. USA 1992, 89, 3010–3014. mRNA from sections and cells was amplified (aRNA) from double-stranded cDNA templates with T7 RNA polymerase (Epicentre Technologies, Madison, Wis.) incorporating [$^{32}$P]CTP. After initial amplification, a broad spectrum of high to low molecular weight mRNAs was detected from sections and individual cells (approximately 1–6 kbp); this spectrum was similar to that of frozen sections and whole live cells. aRNA served as a template for second-round cDNA synthesis, whose product then served as template for a second aRNA amplification incorporating [$^{32}$P]CTP. The radiolabeled aRNA was used as a probe for reverse Northern (slot) blots.

Reverse Northern Analysis

To detect specific mRNAs present in single neurons and giant cells, reverse Northern (slot) blotting was performed with linearized plasmid cDNAs in accordance with well known procedures. The strategy was to select cDNAs which reflected a sample of mRNAs present in individual neurons with either mature or immature phenotype and which would complement the immunohistochemical data. mRNAs included: human nestin; α internexin; low and medium molecular weight neurofilament; Ki-67; cyclin D1; the L- and N-type calcium channels; trkA; the KV1 potassium channel, connexins(CX) 26, 32, and 43; growth-associated protein 43; the synthetic enzyme GAD65; the $\alpha_2, \alpha_3, \alpha_5$ and $\alpha_6$ subunits of the type A γ-aminobutyric acid receptor (GABA receptor); nitric oxide synthase (NOS); GFAP; MAP2; platelet derived growth factor (PDGF); basic fibroblast growth factor (bFGF); nerve growth factor receptor; (NGFR); the α subunit of calcium/calmodulin-dependent protein kinase (CaMKII); and two regions (2- and 3-kbp fragments) of the TSC2 transcript adherent to nylon membranes. Blots were probed with $^{32}$P-labeled aRNA from whole sections or individual cells. Prehybridization (8 hours) and hybridization (24 hours) were in standard saline/phosphate/EDTA (SSPE) buffer containing Denhardt's solution, 50% formamide, 0.1 SDS, and salmon sperm DNA at 200 μg/ml at 42° C. Blots were apposed to film for 24 to 48 hours. Hybridization was detected by densitometry and IMAGEQUANT 3.3 software.

PCR

PCR primers were generated to human nestin cDNA approximately 490 bp apart (sense primer, 5'-AGAGGGGAATTCCTGGAG-3' (SEQ ID NO: 30) and antisense primer 5'-CTGAGGACCAGGACTCTCTA-3' (SEQ ID NO: 31)). After an initial denaturation at 93° C., 35 cycles of 94° C. for 45 seconds, 46° C. for 1 minute, and 70° C. for 2 minutes were performed with a final 5-minute extension at 72° C. in 2 mM $MgCl_2$. PCR products were transferred to nylon membranes and probed with [$^{32}$P] dCTP-radiolabeled human nestin cDNA.

What is claimed:

1. A method of diagnosing a condition associated with an mRNA expression pattern comprising:
    (a) determining an mRNA expression pattern in selected cells, wherein said selected cells are associated with a selected condition, by a method which comprises:
       (i) converting an mRNA population in the selected cells into cDNA;
       (ii) making the cDNA double stranded;
       (iii) linearly amplifying the double stranded cDNA into aRNA; and
       (iv) using the aRNA as a probe to produce an mRNA expression pattern;
    (b) comparing the mRNA expression pattern determined in the selected cells with an mRNA expression pattern of control cells; and
    (c) diagnosing a condition based upon the comparison of the mRNA expression patterns.

2. The method of claim 1 wherein the selected cells are neurons.

3. The method of claim 2 wherein the condition is a neuropsychiatric disorder.

4. The method of claim 3 wherein the condition is fragile X syndrome.

* * * * *

UNITED STATES PATENT AND TRADEMARK OFFICE
CERTIFICATE OF CORRECTION

PATENT NO. : 5,958,688

DATED : September 28 1999

INVENTOR(S) : Eberwine et al.

It is certified that error appears in the above-identified patent and that said Letters Patent is hereby corrected as shown below:

At Col. 1, Line 10, please delete "Nov. 11, 1995" and insert therefor --Nov. 3, 1995--

Signed and Sealed this

Sixth Day of February, 2001

Attest:

Q. TODD DICKINSON

Attesting Officer

Director of Patents and Trademarks